United States Patent [19]
Patchett et al.

[11] 4,401,676
[45] Aug. 30, 1983

[54] NOVEL α-AMINO ACIDS

[75] Inventors: Arthur A. Patchett, Cranford; David Taub, Metuchen, both of N.J.

[73] Assignee: Merck & Co., Inc., N.J.

[21] Appl. No.: 802,390

[22] Filed: Jun. 1, 1977

[51] Int. Cl.$^3$ .................. A61K 31/245; C07C 101/72
[52] U.S. Cl. .................... 424/309; 424/319; 560/40; 560/250; 562/446; 549/214; 549/434; 549/436; 549/444; 549/445
[58] Field of Search ................ 560/40, 250; 424/309, 424/319; 260/519; 562/446

[56] References Cited

U.S. PATENT DOCUMENTS

| | | | |
|---|---|---|---|
| 2,868,818 | 1/1959 | Pfister et al. | 560/40 |
| 3,329,711 | 7/1967 | Hegedus et al. | 560/40 |
| 3,344,023 | 9/1967 | Reinhold et al. | 260/519 |
| 3,488,363 | 1/1970 | Hinkley | 560/40 |
| 3,553,258 | 1/1971 | Kaiser et al. | 560/40 |
| 3,714,241 | 1/1973 | Grenda | 560/40 |
| 3,784,640 | 1/1974 | Okumura et al. | 560/40 |
| 3,801,601 | 4/1974 | Reinhold et al. | 560/40 |
| 3,983,138 | 9/1976 | Saari | 560/40 |
| 4,022,910 | 5/1977 | Suh et al. | 424/319 |
| 4,051,251 | 9/1977 | Stone | 424/319 |

OTHER PUBLICATIONS

Marcotte et al., Biochemistry, 15, 3070–3076, (1976).

Primary Examiner—James H. Reamer
Attorney, Agent, or Firm—Alice O. Robertson; Daniel T. Szura; Gabriel Lopez

[57] ABSTRACT

Novel α-ethynyl- and α-vinyl 3,4-disubstituted phenylalanines are disclosed. The compounds have pharmaceutical activity.

22 Claims, No Drawings

NOVEL α-AMINO ACIDS

BACKGROUND OF THE INVENTION

The present invention is concerned with α-ethynyl- and α-vinyl-3,4-disubstituted phenylalanines and especially the 3,4-dihydroxyphenylalanine species.

α-Methyl-3,4-dihydroxyphenylalanine, particularly its L-isomer, is a known antihypertensive agent. (U.S. Pat. Nos. 2,868,818; 3,344,023).

Novel α-ethynyl- and α-vinyl-3,4-disubstituted phenylalanines have been discovered. These novel alanines have pharmaceutical activity including antihypertensive action.

SUMMARY OF THE INVENTION

α-Ethynyl- and α-vinyl-3,4-di-OR-phenylalanines, esters thereof and their pharmaceutical use.

DESCRIPTION OF THE PREFERRED EMBODIMENTS

The present invention is embodied in α-ethynyl- or α-vinyl phenylalanine compounds having the formula

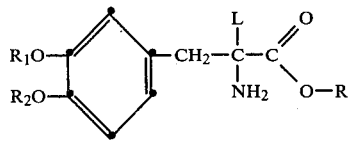

wherein
L is —C≡CH or —CH=CH$_2$,
R$_1$ and R$_2$ are independently selected from H and C$_2$–C$_6$ alkanoyl, and
R is C$_1$–C$_{18}$ alkyl or H.

The pharmaceutically acceptable salts of the formula I compounds are also included. These salts generally are acid addition salts of suitable organic or inorganic acids. Preferred salts are the hydrohalides such as the hydrobromides, the hydrochlorides, the hydrogen iodides. Most preferred salts are the hydrochlorides.

The compounds of formula I have a chiral center and may occur in optically active forms i.e. as optical isomers. These isomers are conventionally designated as D and L, d and l, + and −, (S) and (R) or by a combination of these symbols. Where the compound name or formula does not specify the isomer form, all forms are included i.e. the individual isomers, mixtures thereof and racemates.

Of the isomers, the L-form is preferred.

R may be H or an alkyl group, preferably a C$_1$–C$_{18}$ alkyl group. Examples of suitable alkyl groups are octadecyl, 2-ethylhexyl, lauryl, undecyl, methyl, isopropyl, hexyl and the like. Preferred R groups are H and C$_1$–C$_6$ alkyl. Most preferred R groups are H and ethyl.

R$_1$ and R$_2$ include H and C$_2$–C$_6$ alkanoyl groups. Examples of suitable alkanoyl groups are acetyl, octanoyl, pivaloyl, 2-methylpropanoyl, heptanoyl, butanoyl and the like. The most preferred R$_1$/R$_2$ substituent is hydrogen.

A preferred class of compounds of the present invention is that having the formula

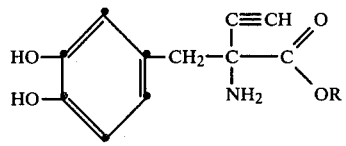

Especially preferred are formula II compounds where R is hydrogen or C$_1$–C$_6$ alkyl, preferably ethyl.

The L-isomer form of the formula II compound is also more preferred.

Another preferred class of compounds of the present invention is that having the formula

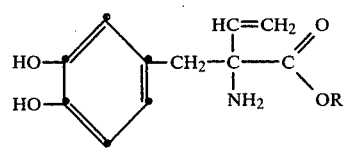

Especially preferred are the formula III compounds where R is hydrogen or C$_1$–C$_6$ alkyl, preferably ethyl.

The L-isomer form of the formula III compounds are also more preferred.

The compounds of the present invention have pharmaceutical activity especially as antihypertensive agents. Thus, the present compounds are useful for treating hypertension in humans.

Other biological activities of the present compounds include inhibition of 3,4-dihydroxyphenylalanine (dopa) decarboxylase.

For treating hypertension, the present compounds may be administered to the hypertensive patient orally, parenterally or via any other suitable administration route. Conventional dosage forms are used such as tablets, troches, capsules, liquid formulations, e.g. solutions, dispersions, emulsions, elixirs and the like. Conventional compounding ingredients i.e. diluents, carriers etc. and conventional preparation procedures are utilized.

The daily dosage of the present compounds may be varied as required. In general, a daily dosage range for the hypertensive patient is about 50 mg. to about 5000 mg. A preferred daily dosage range is about 100 mg. to about 3500 mg. A more preferred daily dosage range is about 250 to about 1500 mg.

Compounds of the present invention may be prepared by any convenient process.

An especially useful process for preparing the compounds of formula I where R is hydrogen is by the hydrolysis of a compound having the formula

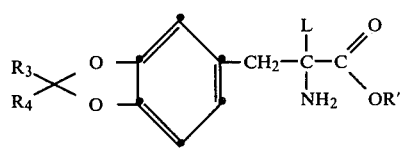

where L is —C≡CH or —CH=CH$_2$, R' is alkyl preferably C$_1$–C$_6$ alkyl, and R$_3$ and R$_4$ are groups e.g. H, CH$_3$ or phenyl, which permit hydrolysis of the dioxy moiety. The hydrolysis is carried out using conventional reagents and conditions, for example using an acid such as HCl, HBr, H$_3$PO$_4$, in a suitable solvent such as water, aqueous alkanols and the like. The hydrolysis may be carried out at room temperature or at elevated temperatures up to about 140° C. The reaction time will vary depending on other parameters such as temperature, etc.

Where R in formula I is an alkyl group, the compound is prepared by conventional esterification of the corresponding compound where R is H as illustrated by the following equation

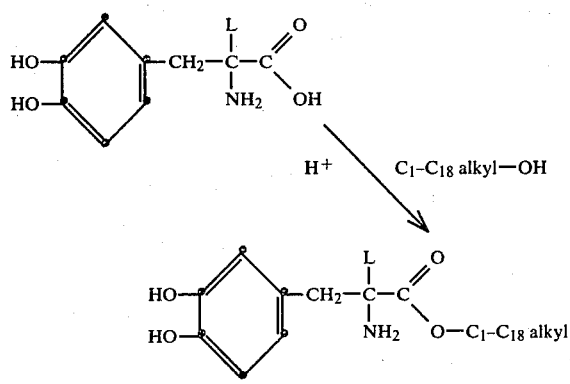

The pharmaceutically acceptable salts of the present compounds may be obtained directly from the hydrolysis reaction described above. Such salts may also be obtained by treatment of the formula I free base with an appropriate acid under suitable conditions.

Where the compounds of the present invention are obtained as racemates, they may be separated into the individual enantiomers by conventional resolution techniques. Such techniques commonly involve the formation of salts of the present racemic acids with optically active bases. The resolution is preferably carried out on the O,O,N-triacyl derivatives of the racemic acid mixture. These acyl derivatives are prepared by treatment of the free acid mixture with a suitable acylating agent as illustrated by the following equation:

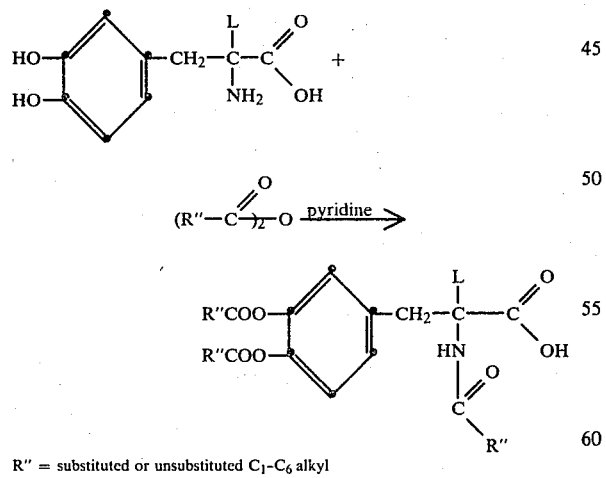

R″ = substituted or unsubstituted $C_1$-$C_6$ alkyl

The resolution procedure including hydrolysis of the resolved acylated acids is exemplified in U.S. Pat. No. 3,344,023.

Compounds of the present invention where $R_1$ and $R_2$ are lower alkanoyl are prepared by appropriately acylating the corresponding compound where $R_1$ and $R_2$ are each H, as illustrated by the following equation:

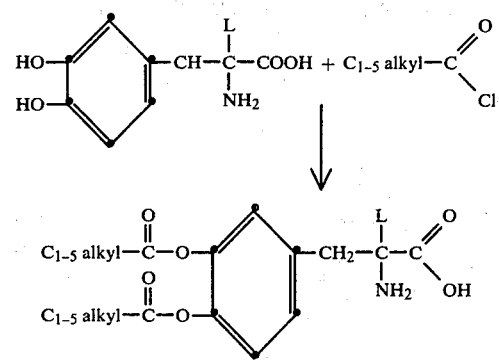

To prevent acylation of the α-$NH_2$ group, the reaction may be carried out in an acid medium e.g. glacial acetic acid. An example illustrating such an acylation system is in U.S. Pat. No. 3,983,138.

The following examples illustrate preparation of compounds of the present invention via a series of intermediate steps. All temperatures are °C. The symbol Ph represents the phenyl group in the formulae below:

EXAMPLE 1

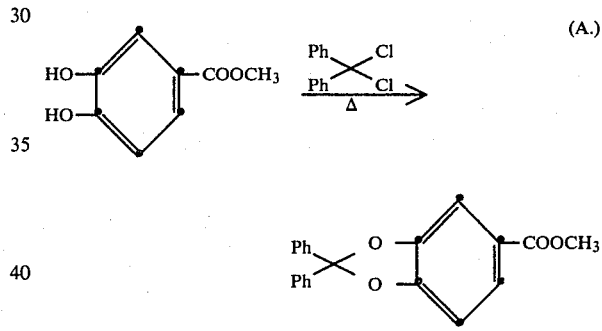

A mixture of methyl 3,4-dihydroxybenzoate (8.40 g.; 50 mmol) and diphenyldichloromethane was stirred at 150±5° for 15 minutes. The mixture was cooled, taken up in benzene and the benzene solution washed with 5% aqueous $KHCO_3$, saturated aqueous NaCl, dried over $MgSO_4$ and concentrated to dryness. The crystalline residue (m.p. 98°–100°) was recrystallized from hexane containing a little benzene to give pure methyl 3,4-diphenylmethylenedioxybenzoate (15.3 g., 96%) m.p. 103°–105°.

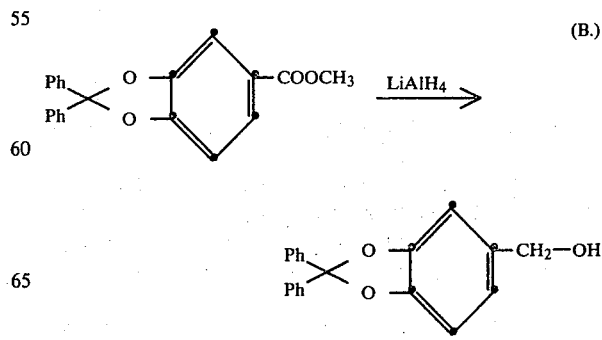

To a stirred suspension of 1.48 g. LiAlH₄ in 80 ml. of ether was added dropwise a solution of methyl-3,4-diphenylmethylenedioxybenzoate (13.09 g.; 39.4 mmol) in 80 ml. ether and 10 ml. tetrahydrofuran. The rate of addition was controlled to maintain the reaction mixture at a gentle reflux. The mixture was then refluxed 45 minutes. It was then cooled and 5 ml. of ethyl acetate was added dropwise followed by 15 ml. of saturated aqueous Na₂SO₄ and about 5 g. anhydrous MgSO₄. The mixture was filtered, the inorganic precipitate washed with 1:1 ether-benzene, and the combined filtrate and washings concentrated to dryness to give 11.65 g. of 3,4-diphenylmethylenedioxybenzyl alcohol as a colorless viscous oil which partially solidified on cooling. On recrystallization from hexane-benzene an aliquot had m.p. 63°-64°.

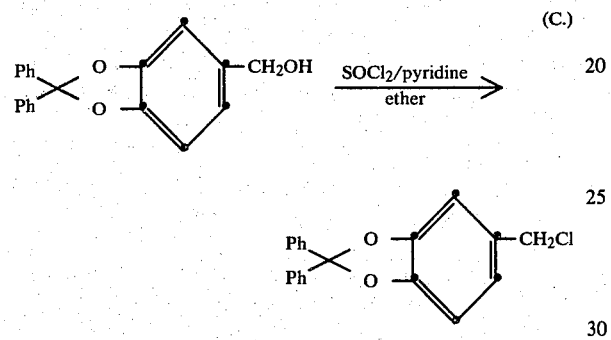

To a stirred solution of 11.6 g. (38 mmol) of 3,4-diphenylmethylenedioxybenzyl alcohol in ether (80 ml.) and pyridine (0.6 ml.) at 20° C. was added dropwise a solution of SOCl₂ in ether (40 ml.). The mixture was cooled to 0°-5° C., and CH₂Cl₂ and water were added. The layers were separated, and the organic layer was washed with water and saturated aqueous NaCl, dried over MgSO₄ and concentrated to dryness to yield 3,4-diphenylmethylenedioxybenzyl chloride (11.43 g.) as a colorless viscous oil: tlc (silica gel CH₂Cl₂: R_f 0.8; ir (CCl₄) no —OH—, nmr (CCl₄) δ 4.34 (s, 2H), 6.74 (d,j=8) 2H, 6.67 (s, 1H), 7.1-7.6 (m, 10H).

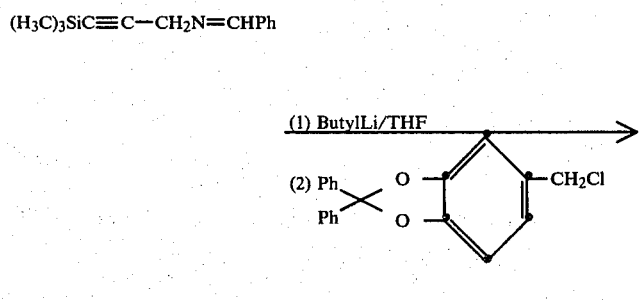

To a stirred solution of 1-trimethylsilyl-N-benzylidene-3-aminoprop-1-yne (7.609 g.; 34.4 mmol) in 106 ml. of tetrahydrofuran maintained at −78° under N₂ was added dropwise 19.5 ml. of 1.63 N n-butyl lithium. To the stirred deep red solution was then added dropwise 11.43 g. (35.4 mmol) of 3,4-diphenylmethylenedioxybenzyl chloride in 35 ml. of tetrahydrofuran. After an additional 30 minutes at −78° water (25 ml.) was added dropwise, the mixture was warmed to 20°, 10% aqueous NH₄Cl solution was added and the layers were separated. The aqueous layer was washed twice with benzene, the combined organic phases were washed twice with cold 10% aqueous NH₄Cl, once with saturated NaCl solution, dried over Na₂SO₄ and concentrated to dryness to give 3-(3,4-diphenylmethylenedioxybenzyl)-1-trimethylsilyl-N-benzylidene-3-aminoprop-1-yne as a viscous orange oil (18,86 g).

The mass spectrum showed a large molecular ion peak at 501.

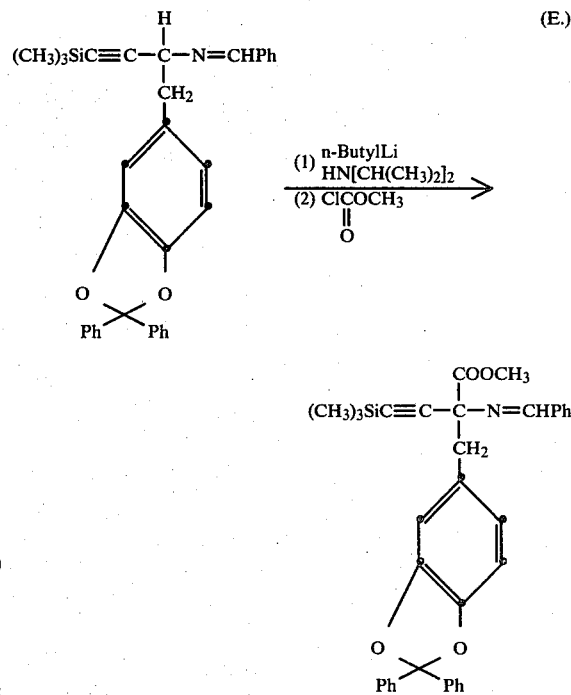

To diisopropylamine (700 mg.) in 15 ml. tetrahydrofuran at −78° under N₂ was added 3.8 ml. of 1.64 M n-butyllithium dropwise. After 5 minutes, 3-(3,4-diphenylmethylenedioxybenzyl)-1-trimethylsilyl-N-benzylidene-3-aminoprop-1-yne (3.378 g.; 6.74 mmol) in 15 ml. tetrahydrofuran was added dropwise (10 minutes). After an additional 5 minutes, methyl chlorofor-

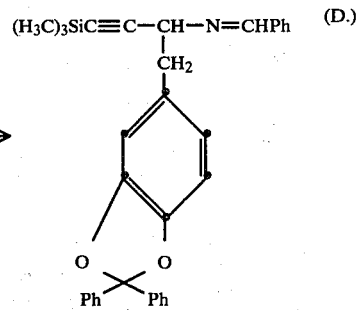

mate (680 mg.) in tetrahydrofuran (10 ml.) was added dropwise (5 minutes). After 40 minutes at −78° the solution was warmed to 0° and the color lightened from deep red to orange. After 10 minutes at 0°, water (5 ml.) was added dropwise followed by 10% aqueous NH₄Cl (30 ml.). The layers were separated and the mixture extracted as in the previous example, dried over Na₂SO₄ and concentrated to dryness to give 3-carbomethoxy-3-(3,4-diphenylmethylenedioxybenzyl)-1-trimethylsilyl-N-benzylidene-3-aminoprop-1-yne (3.645 g.) as an orange foam; Mass spectrum M/e 559, large fragmentation peaks at 287 (base peak) and 272.

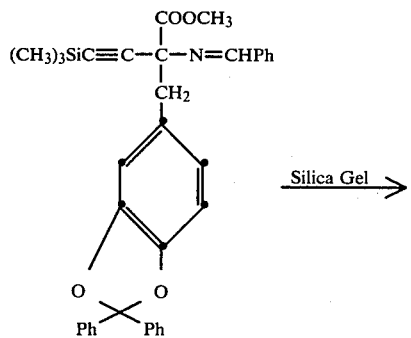

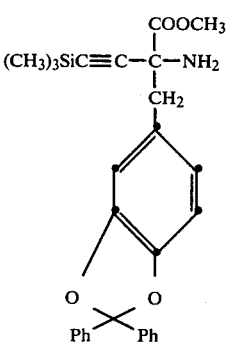

Chromatography of crude 3-carbomethoxy-3-(3,4-diphenylmethylenedioxybenzyl) 1-trimethylsilyl-N-benzylidene-3-aminoprop-1-yne (3.55 g.) over 180 g. of silica gel H eluting with 2% acetone in chloroform led to hydrolysis of the Schiff base protecting group to give the free amine, 3-carbomethoxy-3-(3,4-diphenylmethylenedioxybenzyl)-3-aminopropyl-1-yne (tlc silica gel 3% acetone in CHCl₃ $R_F$~0.2) Mass spec. M/e 471.

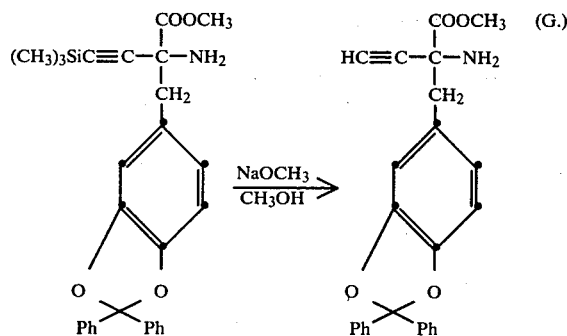

To a solution of 3-carbomethoxy-3-(3,4-diphenylmethylenedioxybenzyl)-1-trimethylsilyl-N-benzylidine-3-aminoprop-1-yne (610 mg.) in 6 ml. of methanol under nitrogen at 20° C. was added 1.1 ml. of 1.6 M NaOCH₃ in CH₃OH. The solution was stirred 30 minutes, CH₂Cl₂ and cold water were added and the layers separated. The aqueous layer was washed with CH₂Cl₂ and the combined CH₂Cl₂ phase washed with cold water and saturated NaCl solution, dried over Na₂SO₄ and concentrated to dryness to give 3-carbomethoxy-3-(3,4-diphenylmethylenedioxybenzyl)-3-aminoprop-1-yne (505 mg.) as a viscous orange foam; nmr (CDCl₃) 1.80 (broad S, 2H) 2.45 (s, 1H) 3.10 (s, 2H), 3.75 (s, 3H) 6.79 (d,j=5,2H), 6.75 (s, 1H), 7.0–7.7 (m, 10H).

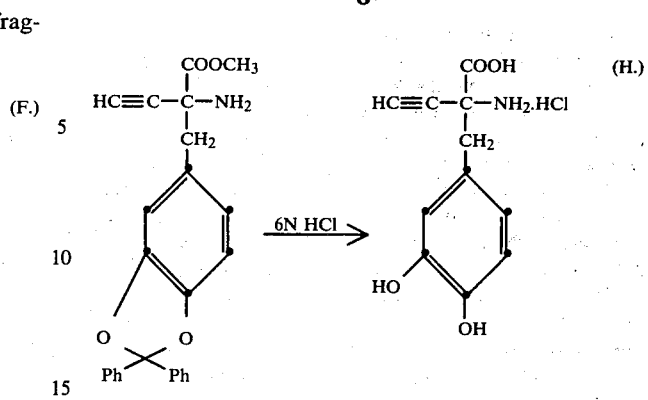

A solution of 3-carbomethoxy-3-(3,4-diphenylmethylenedioxybenzyl)-3-aminoprop-1-yne (230 mg.) in 6 N HCl (15 ml.) was refluxed for 2 hours, cooled and extracted with CH₂Cl₂. The aqueous acid phase was taken to dryness to give α-ethynyl-3,4-dihydroxyphenylalanine hydrochloride (135 mg, 90%) tlc-n butanol:acetic acid:water 25:4:10 single spot $R_F$ 0.4; n-butanol:acetic acid:water:pyridine 15:3:12:10 single spot $R_F$0.6; mass spec. M⁺ 221; (D₂O) δ 3.17 (s, 2H), 3.22 (s, 1H) 6.70 m, 3H).

The HCl salt obtained in Example 1 H.) may be conventionally neutralized or treated with an HCl scavenger such as propylene oxide to obtain the corresponding free amino acid.

EXAMPLE 2

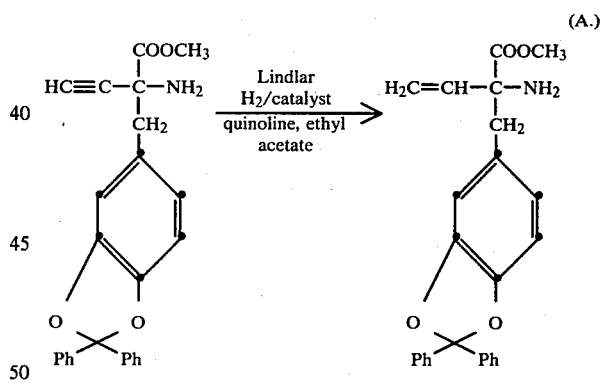

A solution of 3-carbomethoxy-3-(3,4-diphenylmethylenedioxybenzyl-3-aminoprop-1-yne (90 mg.) in 10 ml. of ethyl acetate and 0.02 ml. quinoline was stirred in 1 atm of hydrogen over 20 mg. of Lindlar's catalyst [5%Pd-CaCO₃+Pb(OAc)₂] at 25° until hydrogen uptake ceased. The catalyst was removed by filtration and the filtrate taken to dryness. The nearly pure product, was purified by dry column chromatography on 10 g. of silica gel eluting with 15% acetone in chloroform to give pure 3-carbomethoxy-3(-3,4-diphenylmethylenedioxybenzyl)-3-aminoprop-1-ene, mass spec. M⁺ 401; nmr (CDCl₃) 1.72 (s, 2H), 2.75 (d, J=14, 1H), 3.18 (d, J=14.1H)-AB quartet 3.70 (s, 3H), 5.17 (d,d,J=10,2,1H), 5.35 (d,d,J=18,2,1H) 6.17 (d,d,J=18, 10, 1H) 6.72–677 (m, 3H); 7.25–7,8 (m, 10H).

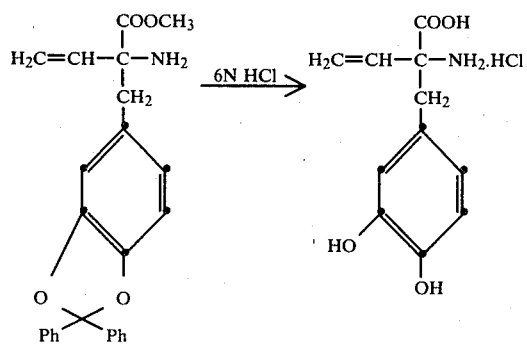

Utilizing the procedure of Example 1 H.), 3-carbomethoxy-3(3,4-diphenylmethylenedioxybenzyl)-3-aminoprop-1-ene was hydrolyzed to produce α-vinyl-3,4-dihydroxyphenylalanine hydrochloride. tlc-n-butanol, acetic acid:water:pyridine-15:3:12:10 single spot $R_F \sim 0.65$; mass spec $M^+$ 223; nmr ($D_2O$) δ 3.03 (d, J=15, 1H), 3,33 (d, J=15, 1H) AB quartet, 5.35 (d, J=18, 1H); 5.50 (d,J=12, 1H), 6.18 (d,d,J=18,12, 1H), 6.6–7.1 (m 3H).

The HCl salt obtained in Example 2 B may be conventionally neutralized or treated with an HCl scavenger such as propylene oxide to obtain the corresponding free amino acid.

What is claimed is:

1. Compounds having the formula

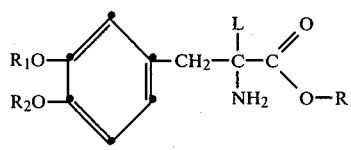

wherein

L is —C≡CH or —CH=CH$_2$,

R$_1$ and R$_2$ are independently selected from H and C$_1$-C$_6$ alkanoyl, and

R is C$_1$-C$_{18}$ alkyl or H.

2. The pharmaceutically acceptable salts of the claim 1 compounds.

3. Compounds of claim 1 having the L-isomer configuration.

4. Compounds of claim 1 wherein R$_1$ and R$_2$ are both hydrogen.

5. Compounds of claim 4 wherein R is hydrogen.

6. Compounds of claim 1 having the formula

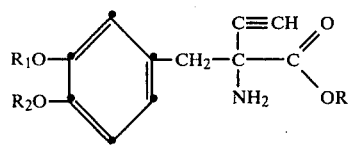

7. Compounds of claim 6 having the L-isomer configuration.

8. Compounds of claim 6 wherein R$_1$ and R$_2$ are both hydrogen.

9. Compounds of claim 6 wherein R is H or C$_1$-C$_6$ alkyl.

10. Compounds of claim 8 wherein R is ethyl.

11. Compounds of claim 8 wherein R is hydrogen.

12. Compounds of claim 11 having the L-isomer configuration.

13. Compounds of claim 1 having the formula

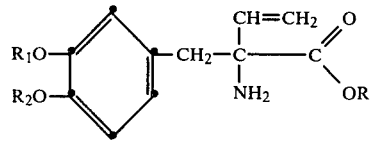

14. Compounds of claim 13 having the L-isomer configuration.

15. Compounds of claim 13 wherein R$_1$ and R$_2$ are both hydrogen.

16. Compounds of claim 15 wherein R is H or C$_1$-C$_6$ alkyl.

17. Compounds of claim 14 wherein R is ethyl.

18. Compounds of claim 16 wherein R is H.

19. Compounds of claim 18 having the L-isomer configuration.

20. An antihypertensive pharmaceutical composition containing a therapeutical effective amount of a compound of claim 1 or a pharmaceutically acceptable salt thereof and a pharmaceutical carrier therefor.

21. A compound of the formula

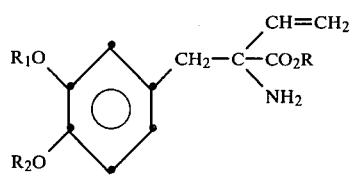

wherein

R is H or C$_1$-C$_8$ alkyl and

R$_1$ and R$_2$ are independently selected from H and alkanoyl of up to C$_6$ and the pharmaceutically acceptable salts thereof.

22. A compound of the formula

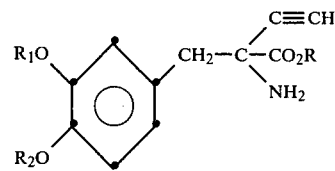

wherein

R is H or C$_1$-C$_8$ alkyl and

R$_1$ and R$_2$ are independently selected from H and alkanoyl of up to C$_6$ and the pharmaceutically acceptable salts thereof.

* * * * *